United States Patent [19]

Koop

[11] Patent Number: 5,360,447
[45] Date of Patent: Nov. 1, 1994

[54] LASER ASSISTED HAIR TRANSPLANT METHOD

[75] Inventor: Dale E. Koop, Sunnyvale, Calif.
[73] Assignee: Coherent, Inc., Santa Clara, Calif.
[21] Appl. No.: 12,895
[22] Filed: Feb. 3, 1993
[51] Int. Cl.$^5$ .............................................. A61F 2/10
[52] U.S. Cl. .......................................... 623/15; 606/9; 606/187; 607/89
[58] Field of Search ................. 623/15; 606/9, 170, 606/187; 607/89; 132/53, 56, 201

[56] References Cited

U.S. PATENT DOCUMENTS

| | | | |
|---|---|---|---|
| 4,144,876 | 3/1979 | DeLeo | 623/15 X |
| 4,388,924 | 6/1983 | Weissman et al. | 606/9 |
| 4,768,517 | 9/1988 | Joachim | 623/15 X |
| 5,123,028 | 6/1992 | Hobart et al. | 372/95 |
| 5,137,533 | 8/1992 | Gianpapa | 623/15 |

*Primary Examiner*—Randall L. Green
*Assistant Examiner*—Mary Beth Jones
*Attorney, Agent, or Firm*—Limbach & Limbach

[57] ABSTRACT

A hair transplant procedure is described which includes preparing a plurality of hair plugs from a donor site on the scalp. A corresponding number of incisions are drilled into the hairless recipient site using a pulsed laser beam. Preferably, the beam is generated from a high power, RF excited, carbon dioxide, slab waveguide laser. The pulse characteristics of the laser are chosen to ablate the tissue to the desired depth while minimizing bleeding. The plugs are inserted into the incision and hair growth in the recipient region is promoted.

14 Claims, 1 Drawing Sheet

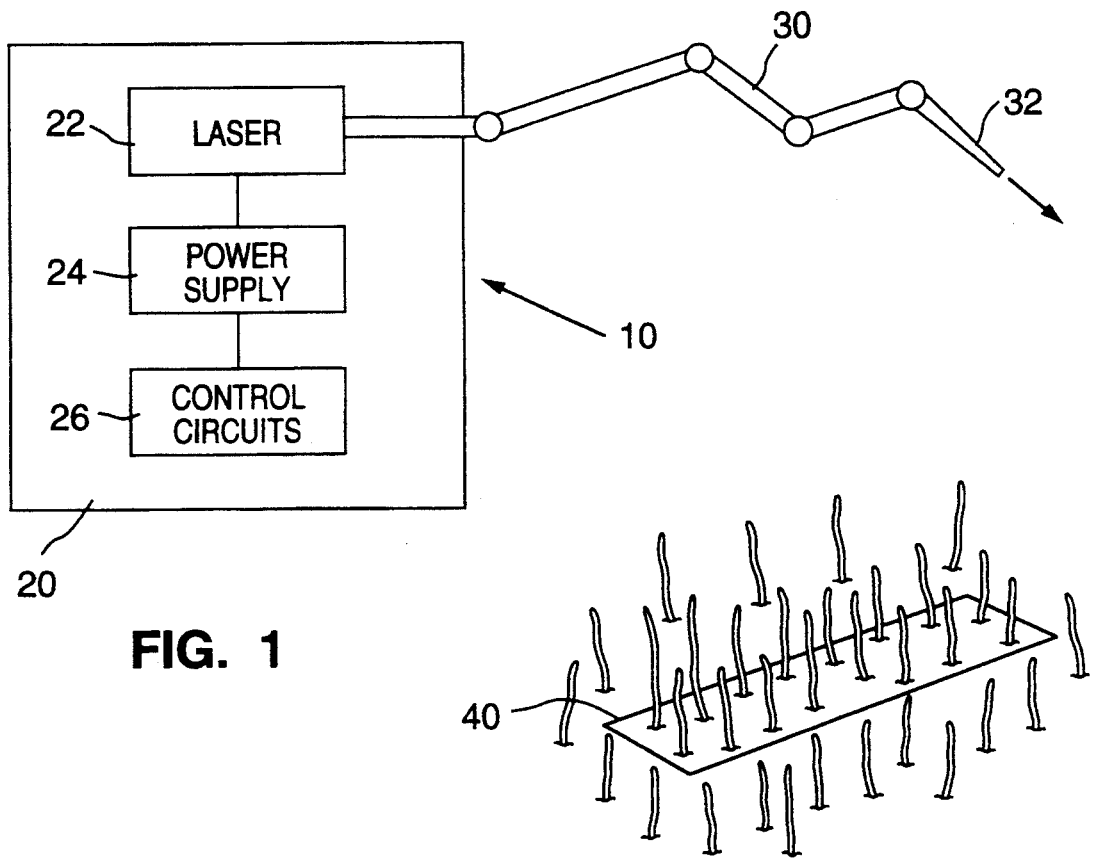
FIG. 1
FIG. 2
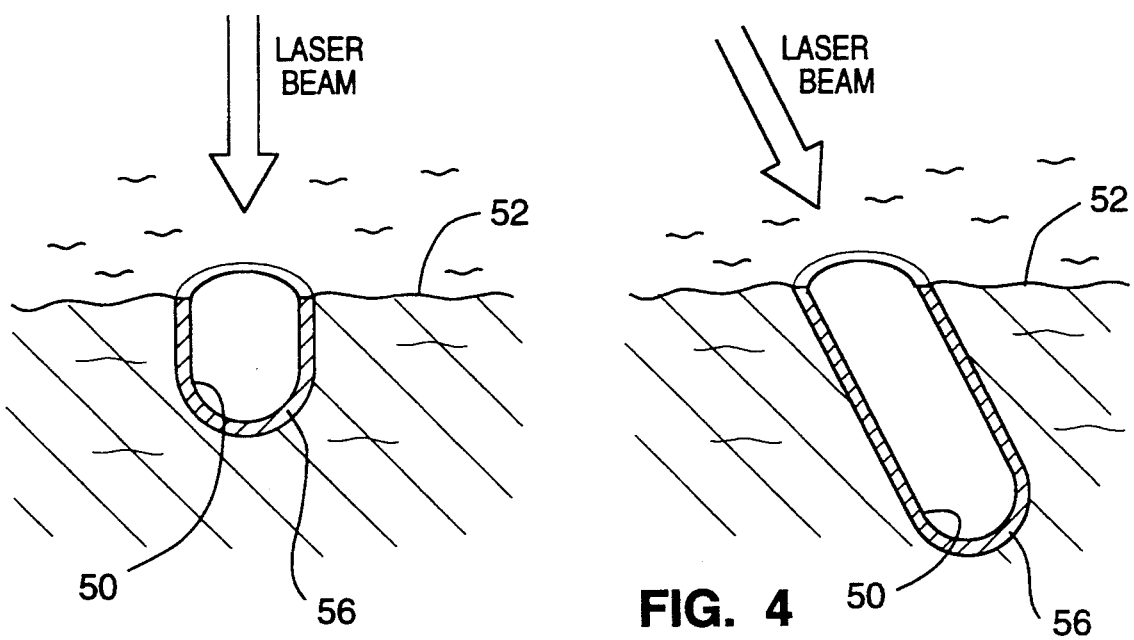
FIG. 3
FIG. 4

LASER ASSISTED HAIR TRANSPLANT METHOD

TECHNICAL FIELD

The subject method relates to a hair transplant method wherein a pulsed laser beam is used to drill holes in the scalp with less pain and bleeding than with prior mechanical methods. Previously harvested hair plugs are inserted into the holes drilled by the laser.

BACKGROUND OF THE INVENTION

Hair transplants have become a common cosmetic procedure, particularly for the treatment of male pattern baldness. In a hair transplant procedure, a piece of the patient's skin having healthy growing hair is removed from a donor region on the scalp and implanted into a hairless, recipient region. Within a few months time, the transplanted hair will begin to grow and survive in a healthy manner.

In earlier hair transplant procedures, a circular cutting punch (trephine) was used to remove a round piece of skin (graft or plug) from the hair bearing donor area. A slightly smaller trephine was used to cut out a circular incision in the recipient area. The graft was then placed into the incision. Approximately 100 grafts were typically transplanted per session, with roughly four sessions being necessary to provide adequate coverage of the bald region in a male patient.

The trend over the last few years has been to utilize a larger number of much smaller grafts. This approach, while more time consuming, has various cosmetic benefits. These smaller grafts typically contain three to six hairs. The grafts can be harvested using a much smaller trephine, on the order of 1.0 to 2.5 mm in diameter. In recipient areas near the hairline, where cosmetic blending is desired, even smaller grafts, having only one to two hairs are used. The incision in the recipient area is made with a #16 gauge hypodermic needle.

Another recent variation to the transplant procedure includes the use of a scalpel blade to form slit incisions in the recipient area. Slit grafting is desirable because the incision can be made between existing hairs.

All of the above described approaches have drawbacks. First, all of the incisions cause scalp bleeding which slows surgery and leads to post surgery crusting and patient discomfort. In addition, for best results, the size and shape of the incision must be accurately controlled, requiring great surgical skill. This desire for accurate incisions is made more complicated since the instruments tend to become dull rather quickly.

A further set of problems are encountered with slit grafting since recipient tissue is not removed as it is when a trephine is used. In order to accommodate the graft, the slit must be longer than the graft. In addition, the graft tends to be compressed into the slit which creates a cosmetically unacceptable appearance.

Accordingly, it would be desirable to develop a new approach to hair transplant surgery which addresses the disadvantages of the prior techniques.

SUMMARY OF THE INVENTION

The problems of the prior art hair transplant procedures are addressed in the subject invention by utilizing a laser beam to create the incisions in the recipient region. In the preferred embodiment, a compact, carbon dioxide laser is used to generate high power pulses for ablating tissue and cauterizing blood vessels. By setting specific pulse characteristics, including power, pulse length and spot size, the surgeon can accurately control the size and depth of the incision and accurately control the extent of hemostasis. In addition, since tissue is removed, slit type incisions can be made while avoiding the prior problems of compression.

To be useful, the laser selected should be compact, portable and capable of generating a high power density, with accurate output controls. The assignee herein markets a suitable medical laser under the trademark "Ultrapulse". The structure of the laser engine within the system is described in detail in commonly owned U.S. Pat. No. 5,123,028, the disclosure of which is incorporated herein by reference and discussed in greater detail below.

In the method of the subject invention, the pulsed laser beam is used to drill a hole of the desired size and depth in the recipient area. The grafts are then inserted into the laser drilled holes. The coagulating effects of the laser radiation minimizes bleeding and pain. This approach also minimizes subsequent crusting and reduces recovery time. In initial experiments, it appears that hair density can be increased as compared with existing mechanical approaches.

As discussed below, the laser can also be used to excise the tissue from the donor region. In this manner, the benefits of the laser can be utilized in both of the key surgical steps.

Further objects and advantages of the subject invention will become apparent based on the following detailed description, taken in conjunction with the drawings in which:

BRIEF DESCRIPTION OF THE DRAWINGS

FIG. 1 is a schematic diagram of the laser system used in conjunction with the subject invention.

FIG. 2 is a diagram illustrating the donor area on the patient's scalp.

FIG. 3 is a cross section of an incision made in the recipient region in accordance with the subject method.

FIG. 4 is a cross section of another type of incision made in the recipient region in accordance with the subject invention.

DETAILED DESCRIPTION OF THE PREFERRED EMBODIMENT

Turning to the FIG. 1, there is illustrated a laser system 10 suitable for use with the subject method for transplanting hair. The system 10 includes a housing 20 holding a laser head 22, power supply 24 and control circuitry 26. The output from the laser head is directed into an articulated arm 30 which consists of a number of segments interconnected by rotatable joints. A handpiece 32 is connected to the distal end of the articulated arm. Handpiece 32 includes a lens (not shown) for focusing the beam. Typically, the lens is spherical in configuration for creating a circular spot in the focal plane. Alternatively, a cylindrical lens could be used to produce a rectangular spot more suitable to slit type incisions.

Although a number of laser systems may be suitable for the subject method, it is believed that the characteristics of the assignee's Ultrapulse laser are particularly attractive. The laser engine 22 in the Ultrapulse system is a compact, sealed, RF excited, carbon dioxide slab waveguide laser. The laser generates a output beam of 10.6 microns when a standard $CO_2$ mixture is employed. Using 60 cm long electrodes, the laser is capable of generating a peak powers of up to 500 Watts and maintaining that peak power over the length of the pulse. Pulse widths of up to a millisecond at repetition rates of 500 Hz can be achieved. Each high energy pulse will act independently to remove a precise and constant amount of tissue. In this manner, the surgeon can accurately control the depth of penetration of the incision. The size of the spot will control the diameter of the incision.

The power level and pulse length would be selected based on the spot size (size of the desired incision) and the level of hemostasis desired. Where the energy density on the tissue is in excess of four joules/cm$^2$, almost all of the energy will be used in the ablation of the skin tissue with almost no thermal damage to the underlying tissue. At this level, there is also limited coagulating effects. By lowering the energy density and increasing the pulse length, complete vaporization can be avoided and hemostasis is increased. By proper selection of these parameters, bleeding can be controlled.

It is believed that suitable set of operating parameters would include pulses having an energy of at least 100 millijoules and preferably 250 millijoule per pulse. The pulse width would be between 0.1 and 1.0 milliseconds. The speed of cutting can be set by the repetition rate. Typical repetition rates would be between fifty and hundred pulses per second (50-100 hZ) which would give an average power of about 10 to 25 watts for 250 millijoule pulses. With these parameters, a one millimeter in diameter hole could be drilled to a depth of about four millimeters in about a tenth of a second.

In the subject hair transplant procedure, a strip of hair 40 from the donor region is first excised as indicated in FIG. 2. The strip of hair bearing skin may be about 3 mm by 15 cm. The laser can be used as a scalpel to make an incision around the strip. While it would be preferable to operate the laser in the pulsed mode for this portion of the procedure, the laser could also be run in a CW mode. The hemostatic effects of the laser results in minimal bleeding at the site. The strip is then lifted from the scalp and sutures are used to close the opening.

The strip is then divided into plugs of the desired size. Depending upon the cosmetic effect, each plug can preferably have anywhere from one to six hairs. Of course, the hair plugs could be individually harvested from the donor area using mechanical tools in a manner similar to the prior art.

The laser is then used in the pulsed mode to make incisions 50 in the recipient area 52. As shown in FIGS. 3 and 4, the depth and diameter of the hole can be accurately controlled. The longer hole in shown in FIG. 4 can be made with multiple pulses. As also seen in FIG. 4, the incisions can be formed at an angle to improve retention of the graft and to form a more cosmetically suitable appearance. The energy density level is selected to create a hemostatic region 56 around each hole 50.

It should also be noted that the desired energy density level results in the removal of tissue, similar to the use of a trephine. In this manner, the compression effects which are encountered when using a scalpel to make slit incisions do not occur. In addition, and unlike the prior art, the slits do not have to be made longer than the length of the grafts resulting in less trauma to the recipient area and less injury to the blood supply. A further advantage to using a laser is that since hairless tissue is being removed at the recipient site, greater hair density can be achieved as compared to the prior art slit approaches which did not remove any hairless skin.

The pattern and number of grafts used by the surgeon should be comparable to prior mechanical procedures. However, in view of the advantages achieved with laser incisions, more use can be made of smaller circular grafts and slit grafts.

While the subject invention has been described with reference to a preferred embodiment, various changes and modifications could be made therein, by one skilled in the art, without varying from the scope and spirit of the subject invention as defined by the appended claims.

I claim:

1. A method of implanting a hair graft into the scalp of a patient comprising the steps of:
   incising a region of scalp tissue using a laser beam; and
   inserting the hair graft into the incised region.

2. A method of implanting a hair graft into the scalp of a patient comprising the steps of:
   drilling a hole in the scalp tissue with a pulsed, carbon dioxide laser beam, with the energy density being selected to ablate tissue and reduce bleeding; and
   inserting the hair graft into the hole.

3. A method of implanting a hair graft into the scalp of a patient comprising the steps of:
   generating a pulsed laser beam;
   delivering the beam to a spot on the scalp of the patient, with the spot size, pulse length and power of the beam being selected to incise the tissue and coagulate blood vessels; and
   inserting the hair graft into the incision.

4. A method as recited in claim 3 wherein said incision is a circular hole.

5. A method as recited in claim 3 wherein said incision is a slit.

6. A method as recited in claim 5 wherein said slit is 1 to 2 mm wide.

7. A method as recited in claim 3 wherein the incision is formed at an angle which is offset from a perpendicular with respect to the scalp surface.

8. A method as recited in claim 3 wherein the pulses in said laser beam have an energy of at least 100 millijoules and a length of between 0.1 and 1.0 milliseconds.

9. A method of transplanting hair from a donor area on the scalp of a patient to a hairless recipient area on the scalp of the patient comprising the steps of:
   removing a strip of skin having hair from the donor area;
   dividing the strip into a plurality of plugs each containing one or more hairs;
   drilling a plurality of holes in the recipient area, said holes being drilled using a pulsed, carbon dioxide laser having pulse characteristics selected to ablate tissue while minimizing bleeding; and
   inserting a plug into each hole.

10. A method as recited in claim 9 wherein each of said holes is circular.

11. A method as recited in claim 9 wherein each of said holes is in the form of a slit.

12. A method as recited in claim 11 wherein said slit is 1 to 2 mm wide.

13. A method as recited in claim 9 wherein each hole is formed at an angle which is offset from a perpendicular with respect to the scalp surface.

14. A method as recited in claim 9 wherein each of the laser pulses have an energy of at least 100 millijoules and a length of between 0.1 and 1.0 milliseconds.

* * * * *